United States Patent
Yang

(10) Patent No.: US 9,086,416 B2
(45) Date of Patent: Jul. 21, 2015

(54) **REMOVABLE SACCHARIDE-BENZIMIDAZOLE (BIM) TAGS AND CONJUGATES THEREOF VIA 1*H*-POSITION OF THE BENZIMIDAZOLES**

(75) Inventor: Wen-Bin Yang, Shenkeng Township (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/548,181

(22) Filed: Jul. 12, 2012

(65) Prior Publication Data
US 2013/0102049 A1 Apr. 25, 2013

Related U.S. Application Data

(60) Provisional application No. 61/643,280, filed on May 5, 2012, provisional application No. 61/506,775, filed on Jul. 12, 2011.

(51) Int. Cl.

| | |
|---|---|
| *A61K 31/70* | (2006.01) |
| *A61K 31/7028* | (2006.01) |
| *A61K 31/7042* | (2006.01) |
| *C07H 15/00* | (2006.01) |
| *C07H 15/04* | (2006.01) |
| *C07H 17/00* | (2006.01) |
| *G01N 33/58* | (2006.01) |
| *C07H 15/26* | (2006.01) |
| *G01N 33/531* | (2006.01) |

(52) U.S. Cl.
CPC ............... *G01N 33/58* (2013.01); *C07H 15/26* (2013.01); *G01N 33/531* (2013.01); *Y10T 436/14* (2015.01)

(58) Field of Classification Search
USPC .................... 514/25, 17.4; 536/4.1, 17.4, 124
See application file for complete search history.

(56) References Cited

U.S. PATENT DOCUMENTS

| 3,849,431 A | * | 11/1974 | Bosshard et al. | ............ 540/603 |
| 2007/0048182 A1 | * | 3/2007 | Song et al. | ....................... 422/61 |
| 2007/0054304 A1 | * | 3/2007 | Agnew et al. | ..................... 435/6 |
| 2010/0311654 A1 | * | 12/2010 | Roy et al. | ....................... 514/9.7 |

OTHER PUBLICATIONS

Lin et al. (Molecules 2010, 15, 1340-1353).*
Panagopoulos et al. (Chim. Chronika (Athens, Greece), Spec. Ed. (1957) 72-78) (Abstract sent).*

* cited by examiner

*Primary Examiner* — Shaojia Anna Jiang
*Assistant Examiner* — Michael C Henry
(74) *Attorney, Agent, or Firm* — Shantanu Basu; Eckman Basu LLP

(57) ABSTRACT

Novel method and reagents for generating reversibly tagged saccharides, aldehydes, carboxyl acids, or orthoacetates useful in analytical and diagnostic applications are disclosed. Saccharides are coupled at the reducing end to tagging moieties comprising a reagent selected from a ortho-diaminobenzoic (DAB)-peptide, an aldo-imidazole or N-methylated aldo-imidazole, or an ortho-phenyldiamine (OPD) or substituted OPD. The tagged saccharide further comprising detectable or functional groups coupled to the tagging moiety are provided. Kits and reagents for chromatography and mass spectrometry are disclosed.

7 Claims, 15 Drawing Sheets

R = H, biotin, FITC, protein and others
Peptide = His, Lys, Asp and others

REMOVABLE SACCHARIDE-BENZIMIDAZOLE (BIM) TAGS AND CONJUGATES THEREOF VIA 1H-POSITION OF THE BENZIMIDAZOLES

CROSS-REFERENCE TO RELATED APPLICATIONS

This application claims priority of U.S. provisional patent application Ser. No. 61/643,280, titled "DIAMINOBENZOIC OR ORTHO-PHENYLENE DIAMINE CONJUGATED PEPTIDES AS FUNCTIONAL SACCHARIDE TAGGING REAGENTS" filed May 5, 2012, and U.S. provisional patent application Ser. No. 61/506,775, titled "ALDOMEIMS, NEW REMOVABLE SACCHARIDE TAGS" filed Jul. 12, 2011, the contents of which are incorporated herein in their entirety by reference.

TECHNICAL FIELD OF THE INVENTION

This invention relates to the field of carbohydrate analysis. In particular, the invention relates to the field of labeling polysaccharides with detectable tags for analytical and diagnostic applications. More particularly, the invention relates to removable saccharide-benzimidazole (BIM) tags and conjugates thereof with other functional groups and derivatives at the 1H-position of the saccharide-BIM tags.

BACKGROUND OF THE INVENTION

Glycan analysis is increasingly applied in biological research, clinical analysis, and pharmaceutical/biotechnological production methods. Specific glycosylation patterns have been associated with states of health and disease. (Peracaula R, et al. (2003) Glycobiology 13:457-470; Saldova R et al., (2007) Glycobiology 17:1344-1356).

Saccharides play essential biological function, for instance, O-, N-glycans in glycoproteins, O-/M-antigens in lipopolysaccharides (LPS). However, saccharides are difficult to separate and measure in nature due to lack of chromophores and low ionization ability in mass spectrometry (MS). Thus, saccharides are undetectable by conventional photometric methods (e.g. UV/fluorescence in liquid chromatography) or MS analysis. (Price N P J et al., *Anal. Chem.* 2010, 82, 2893; Pabst M. et al., *Anal. Biochem.* 2009, 384, 263; Tripathi, R. P., et al. *Current Org. Chem.* 2008, 12, 1093; Bigge J. C., et al., *Anal. Biochem.* 1995, 230, 229; Harvey, D. J. *J. Chromatogr. B* 2011, 879, 1196; Hase S. et al., *J. Biochem.* 1984, 95:197)

Saccharide labeling is an important topic in analytical chemistry. (Ruhaak L R et al., *Anal Bioanal. Chem.* 397: 3457-3481 (2010)). Although some methods have been developed for saccharide labeling, these approaches suffer from some drawbacks. (Lin, C et al., *J. Org. Chem.* 2008, 73, 3848-3853; Lin, C et al., *Rapid Commun Mass Spectrom.* 2010, 24, 85-94; Lin, C et al., *Molecules* 2010, 15, 1340-1353; Lin, C et al., *Molecules* 2011, 16, 652-664; Chang, Y. L et al., *J. Mass Spectrom.* 2011, 46, 247-255; Kuo C-Y et al., *Molecules* 2011, 16, 1682-1694). An example is the tagging of free saccharides by reductive amination with amino-phospholipids or with neutral or acidic fluorescent reagents. (Hase S. et al., *J. Biochem.* 95:197-203 (1996)). Although this approach is useful and practical in some applications, fractionation of saccharides tagged by these methods has certain limitations.

Conjugation (covalent coupling) of polysaccharides to proteins or peptides has been used previously. Coupling polysaccharide fragments to proteins or peptides through their reducing end by direct reductive amination leads to poor incorporation of the saccharides.

Although there are some successful methods in saccharide labeling as discussed above, these previously reported methods still have some limitations. For example, using these previously reported methods, O-/N-glycans, which are novel and tiny from cellular source, do not reverse for biological assay after reductive amination or C-glycosylation labeling. Actually, the tagged saccharides might have different biological effects from native saccharides. In addition, the labeling reactions through N-condensation (ex. oximes and hydrazones) are reversible process between both tagged and untagged saccharides in acidic conditions (FIG. 1). This physical phenomenon makes them unstable and results in incomplete tagging during reaction and storage.

Thus, there is a long-felt need for a stable, removable tag in glycan chemistry.

SUMMARY OF THE INVENTION

Therefore, suitably labeled saccharides with a UV or fluorescent tagging reagent at reducing end of saccharides are desirable for their analysis using chromatographic or mass methods, and the ortho-phenyl diamine (OPD) and substituted OPD tagging reagents can tag saccharide to form new saccharide-BIM tags, and these tags allow further application to conjugate with other functional groups and derivatives at the 1H-position of the saccharide-BIM tags to form conjugated saccharide-BIMs (saccharide-R-BIMs) suitable for photometric analysis.

The present disclosure is based on a number of newly designed tagged saccharides useful in analytical, medicinal and diagnostic application.

Accordingly, one aspect of the present disclosure relates to modified glycosides having the formula Y-X wherein Y represents a monosaccharide, oligosaccharide or polysaccharide subunit, in which the subunit is linked in a linear or branch chain by glycosidic linkages, and wherein X represents a tagging moiety comprising a ortho-phenyl diamine (OPD) or substituted OPD, in which the substituted groups are benzyl, benzoyl, carbonyl, $NO_2$, F, Cl, Br, I, SH, OH, NH etc.

Described herein the OPDs comprise an ortho-phenyl diamine (OPD) or substituted OPD units, or the ortho-aminophenol, ortho-aminothiophenol etc. The tagged benzimidazole (BIM) derivatives (saccharide-BIMs) can be generated by coupling an OPD tagging reagent to a reducing end of saccharide.

In some embodiments, the OPD tagging reagent is selected from the group consisting of OPD, or substituted OPD, in which the substituted groups are benzyl, benzoyl, carbonyl, $NO_2$, F, Cl, Br, I, SH, OH, NH etc.

In some embodiments, the OPD is generated by ortho-phenyl diamine, ortho-aminophenol, ortho-aminothiophenol or other functional groups with ability to react with saccharides (aldose, sialic acids) or aldehydes.

In some embodiments, the saccharide subunits, Y, are the same or different and are selected from the group consisting of glucose, galactose, fructose, ribulose, mannose, ribose, arabinose, xylose, lyxose, allose, altrose, gulose, rhamnose, arabinose, fucose, N-acetylgalactosamine, glucuronic acid, galacturonic acid, Globo H, GD2, GD3, GD1a, GQ1b, GT1b, GT1a, Gb3, Gb5, SSEA oligosaccharides, Fucosyl GM1, GM2, GM3, blood group antigens (A, B, O, H), Forssman antigens, Lewis a, Lewis b, Lewis X, Sialyl Lewis X, Lewis Y, lactose based O-glycans, N-acetylglucosamine core structures, sialyllactose, sialylated oligosaccharides, sulphated oligosaccharides, phosphated oligosaccharides, manno-oligosaccharides, cello-oligosaccharides, xylo-oligosaccharides, chito-oligosaccharides, malto-oligosaccharides and polysaccharides.

In some embodiments, the tagged products (saccharide-BIMs) further comprise a functional label at 1H-position of saccharide-BIM, wherein the functional label is a solid supporting, dye or alkyl group suitable for photometric analysis.

In some embodiments, the detectable label is selected from the group consisting of BODIPY Dyes, Cascade Blue Dyes, Coumarin, Fluorescein (FITC/FAM), Haptens, Lissamine Rhodamine B Dyes, NBD, Oregon Green Dyes, Texas Red Dyes, bimane azide, Marina Blue, Pacific Blue, Rhodamine 6G Dyes, Rhodamine Green Dyes, Rhodamine Red Dyes, Tetramethylrhodamine, DNP, Digoxigenin, biotin, avidin, streptavidin, protein, luciferin, an anti-dye antibody, carboxyfluorescein, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, DNP, biotin, digoxiginin, horse radish peroxidase (HRP), alkaline phosphatase (AP), β-galactosidase (GAL), glucose-6-phosphate dehydrogenase, β-N-acetylglucosamimidase, β-glucuronidase, invertase, Xanthine Oxidase, firefly luciferase, glucose oxidase, luminol, isoluminol, acridinium esters, 1,2-dioxetanes and pyridopyridazines.

In some embodiments, the functional label is a detectable label suitable for mass spectrometric (MS) or enzymatic analysis of saccharides.

In some embodiments, the functional labeled saccharide-BIM at 1H-position by N-alkylation comprise a fluorescent labels, enzyme labels, radioisotopes, luminescent labels, bioluminescent labels, polymers, metal particles, saccharides, alkyl groups, antibodies, and dyes.

In some embodiments, the functional labeled saccharide-BIMs at 1H-position by N-alkylation are selected from methylation to form conjugated saccharide-BIMs (saccharide-R-BIMs).

In some embodiments, the modified glycoside, Y-X, is coupled to a solid support at 1H-position of saccharide-BIMs, wherein the solid support is selected from a resin, a bead, a planar support, a glass slide, a polycarbonate slide, a nanoparticle, a chromatography medium, a magnetic particle and a metal.

Another aspect of the present disclosure relates to a kit for photometric analysis of saccharides, the kit comprising a composition mentioned above.

Another aspect of the present disclosure relates to a kit for chromatographic separation of saccharides, the kit comprising a composition mentioned above.

Another aspect of the present disclosure relates to a method for preparing a tagged saccharide of the formula: Y-X, wherein Y represents an aldehyde, carboxyl acid, trimethyl o-acetate, alkyled orthocetate, monosaccharide, oligosaccharide or polysaccharide subunit, and wherein X represents a tagging reagent comprising an ortho-phenyl diamine (OPD) or substituted OPD, the method comprising the steps: (1) providing an OPD tagging reagent; and (2) coupling the OPD tagging reagent to a saccharide in the presence of iodine as catalyst and an acidic solvent; (3) further conjugating functional label at 1H-position of saccharide-BIM, wherein the functional label is a solid supporting, dye or alkyl group suitable for photometric analysis; and (4) removing tagged saccharide by reduction and hydrolysis (NaBH$_4$ and acid) for saccharide recovery.

In some aspects, the method mentioned above further comprises a step by coupling the tagged saccharide to a solid support. In some examples, the method mentioned above further comprises a step by coupling the saccharide-BIM tag to a solid support at 1H-position of saccharide-BIM tag.

In some embodiments, the solid support is selected from a resin, a bead, a planar support, a glass slide, a polycarbonate slide, a nanoparticle, a chromatography medium a magnetic particle and a metal.

Another aspect of the present disclosure relates to a method for preparing an ortho-phenyl diamine (OPD) tagging reagent, the method comprising the steps (1) providing OPD or substituted OPDs (e.g. 4,5-dichloro-o-phenylenediamine; 4-methyl-o-phenylenediamine; 4-chloro-5-methyl-o-phenylenediamine; 4-chloro-5-nitro-o-phenylenediamine; 5-bromo-3,4-dimethyl-o-phenylenediamine; 4-nitrile-o-phenylenediamine; ethyl-3,4-diaminobenzoate; 1,2-diaminobenzophenone; 3,4-diaminobenzophenone; 4,5-diamino-6-hydroxy-2-mercaptopyridine; 3,4-diaminofurazen; 2,3-diaminophenazine; 2,3-naphthalenediamine; 1,2-diphenylethylenediamine; 2-aminophenol; 2-amino-3-nitrophenol; 2,3-diaminophenol; 2-aminothiophenol; diaminomaleonitrile; 2,3-diaminopyridine; 3,4-diaminopyridine; 4,5-diaminopyridine; 2,3-diamino-5-chloropyridine; 2,3-diamino-5-bromopyridine; etc.); (2) providing a saccharide (glucose, galactose, fructose, ribulose, mannose, ribose, arabinose, xylose, lyxose, allose, altrose, gulose, rhamnose, arabinose, fucose, N-acetylgalactosamine, glucuronic acid, galacturonic acid, Globo H, GD2, GD3, GD1a, GQ1b, GT1b, GT1a, Gb3, Gb5, SSEA oligosaccharides, Fucosyl GM1, GM2, GM3, blood group antigens (A, B, O, H), Forssman antigens, Lewis a, Lewis b, Lewis X, Sialyl Lewis X, Lewis Y, lactose based O-glycans, N-acetylglucosamine core structures, sialyllactose, sialylated oligosaccharides, sulphated oligosaccharides, phosphated oligosaccharides, manno-oligosaccharides, cello-oligosaccharides, xylo-oligosaccharides, chito-oligosaccharides, malto-oligosaccharides and polysaccharides or aldehyde, carboxyl acid, trimethyl o-acetate, alkyled orthoacetate subunits); (3) conjugating functional label at 1H-position of saccharide-BIMs, wherein the functional label is N-alkylation to solid supporting, dye or alkyl group suitable for application and analysis; and (4) removing tagged saccharides (saccharide-BIMs or saccharide-R-BIMs) to native saccharides by reduction and hydrolysis (NaBH$_4$ and acid) for saccharide recovery.

In some embodiments, the functional label at 1H-position of saccharide-BIM comprises a detectable label selected from fluorescent labels, enzyme labels, radioisotopes, luminescent labels, bioluminescent labels, polymers, metal particles, antibodies, and dyes.

In some embodiments, the functional label at 1H-position of saccharide-BIM is selected from methylation, amination or alkylation.

Another aspect of the present disclosure relates to a method for chromatographic isolation of saccharides, the method comprising the steps: (1) tagging the saccharide with an OPD or substituted OPD tagging reagent in the presence of iodine as catalyst and acidic solvent; (2) assay, measurement or enzymatic digestion of tagged saccharide (saccharide-BIM tag); and (3) subjecting a composition comprising the saccharide to chromatography.

Another aspect of the present disclosure relates to a method for enhancing mass intensity of a saccharide during mass spectrometry (MS), the method comprising the steps: (1) tagging the saccharide with an OPD or substituted OPD tagging reagent in the presence of iodine as catalyst and acidic solvent; and (2) analyzing a composition comprising the saccharide by mass spectrometry, wherein the mass intensity of the tagged saccharide is enhanced.

BRIEF DESCRIPTION OF THE DRAWINGS

The following drawings of schemes and figures form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Figure 1:
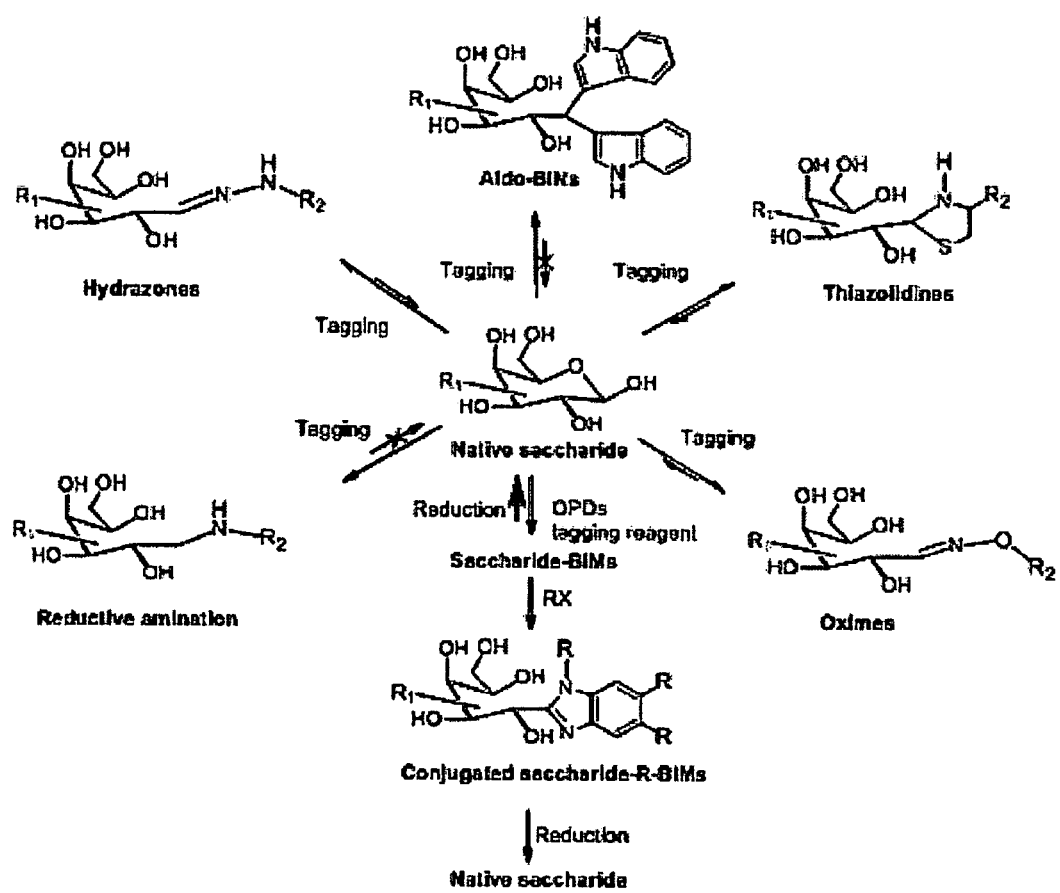
FIG. 1 shows methods for generating saccharide tags in saccharide labeling.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

Disclosed herein are modified glycosides (saccharide-BIM derivatives), the composition comprising (1) a saccharide, aldehyde, carboxyl acid, or alkyl orthoacetate unit, and (b) a tagging moiety comprising an aromatic ortho-diamine unit.

The tagging moiety comprises an ortho-substituted, diamino-aromatic compound. In different embodiments of the invention the ortho-substituted, diamino-aromatic compound is 1,2-diaminobenzene (also known as ortho-phenylenediamine; OPD), 3,4-diaminobenzoic acid or 2,3-diaminopyridine. In a preferred aspect, the tagging moiety comprises 3,4-diaminobenzoic acid peptide (DAB-peptide) conjugate.

The term "saccharide" as used herein is used in their broadest sense to refer to saccharides comprising a plurality of repeating units, including, but not limited to saccharides having from 2 to over 2,00 repeating units. Typically, as accepted in the art and as used herein, the term "polysaccharide" refers to a saccharide having from about 10 to about 200 or more repeating units. As accepted in the art and as used herein, the term "oligosaccharide" refers to a saccharide having from about 2 to about 10 repeating units. In certain embodiments, the repeating unit is 1 or more monosaccharide molecules. In accordance with the methods of the invention, fragments of polysaccharides or oligosaccharides from differing types and/or strains of bacteria may be chemically joined or synthetically synthesized to form a saccharide-BIM comprising multiple epitopes from the multiple types and/or strains of bacteria from which the fragments were originally derived and/or identified; accordingly, the composition of the repeating unit(s) of the polysaccharide or oligosaccharide of the invention need not be constant over the entire saccharide chain. The polysaccharides or oligosaccharides encompassed by the methods of the invention comprise one or more amino sugars. In certain embodiments, said one or more amino sugar is a component of the repeating unit of the polysaccharide or oligosaccharide. In other embodiments, the said one or more amino sugar is not a component of the repeating unit of the polysaccharide or oligosaccharide.

The tagging reagent (ortho-diamine, OPD, substituted OPDs) can be made by any conventional methods, e.g., purchased from commercial source. Attaching saccharide-BIM to solid supporting by N-alkylation at 1H position of saccharide-BIM is well known to any one of ordinary skill in the art. For example, a resin, a bead, a planar support, a glass slide, a polycarbonate slide, a nanoparticle, a chromatography medium, a magnetic particle and a metal.

The term "removable" used herein refers to a tagged saccharide (saccharide-BIM or saccharide-R-BIM), which composed of OPD unit and saccharide units can be removed by reduction and hydrolysis to untagged/native saccharide. Preferably, each of the tagged saccharide described herein can be reversed back to unconjugated/native saccharide and OPD tagging reagent by hydrolysis.

This invention for the first time discloses a removable saccharide tag (e.g. saccharide-BIM and saccharide-R$_2$-BIM tags) using OPD and substituted OPDs as tagging reagents with saccharides. After application the used saccharide-BIM and saccharide-R$_2$-BIM tags can be treated by reduction and hydrolysis to give native saccharide and OPD tagging reagent. The native saccharides can be followed through an HPAED-PAD or NMR analysis directly to evaluate the recovery yields of saccharides with no further purification. In addition, using HPAEC-PAD, a series of saccharides was recovered from saccharide-BIMs or saccharide-R$_2$-BIMs (Table 1) and these saccharides have same retention times, spectrum and mass with original native saccharides.

TABLE 1

Measurement of the recovery yields of native saccharides from saccharide-BIMs or saccharide-R$_2$-BIMs by HPAEC-PAD[a].

| Aldose | Times | | | |
|---|---|---|---|---|
| | Native aldose Peak time (min) | Aldo-BIM[a,b] Peak time (min) | Aldo-MeBIMs[c,d] Peak time (min) | Recovery yield (%)[e] |
| Glucose | 12.1 | 7.3[a] | 4.5[c] | 52 |
| Glucose | 12.1 | 6.5[b] | 4.0[d] | 45 |
| Galactose | 8.7 | 7.1[a] | 4.7[c] | 48 |
| Mannose | 13.8 | 8.8[a] | 4.8[c] | 46 |
| Fucose | 4.8 | 2.2[a] | 2.0[c] | 30 |

[a]Peak retention times of aldo-NAIM (naphthylimidazole).
[b]Peak retention times of aldo-BIM (benzimidazole).
[c]Peak retention times of aldo-Me-NAIM.
[d]Peak retention times of aldo-Me-BIM.
[e]Dionex CarboPac PA-10 column was used, eluent 1.25 ml/min in 18 mM NaOH. The sample loading is set at 1 μM.

These removable saccharide tags are useful in biological investigation for the comparison with other types of saccharide tags as shown in FIG. 1.

The tagging reagents, OPD and substituted OPDs, described herein can be used as detectable labels and are capable of for labeling saccharides at reducing end to form saccharide-BIMs, thereby facilitating saccharide purification and analysis. In addition, these saccharide-BIMs or conjugated saccharide-BIMs (saccharide-R$_2$-BIM) can increase ionization ability of saccharides, thereby improving sensitivity in MS analyses. The tagged/conjugated saccharide described herein can be reversed back to untagged/unconjugated saccharide and OPD by reduction and hydrolysis.

Figure 2:
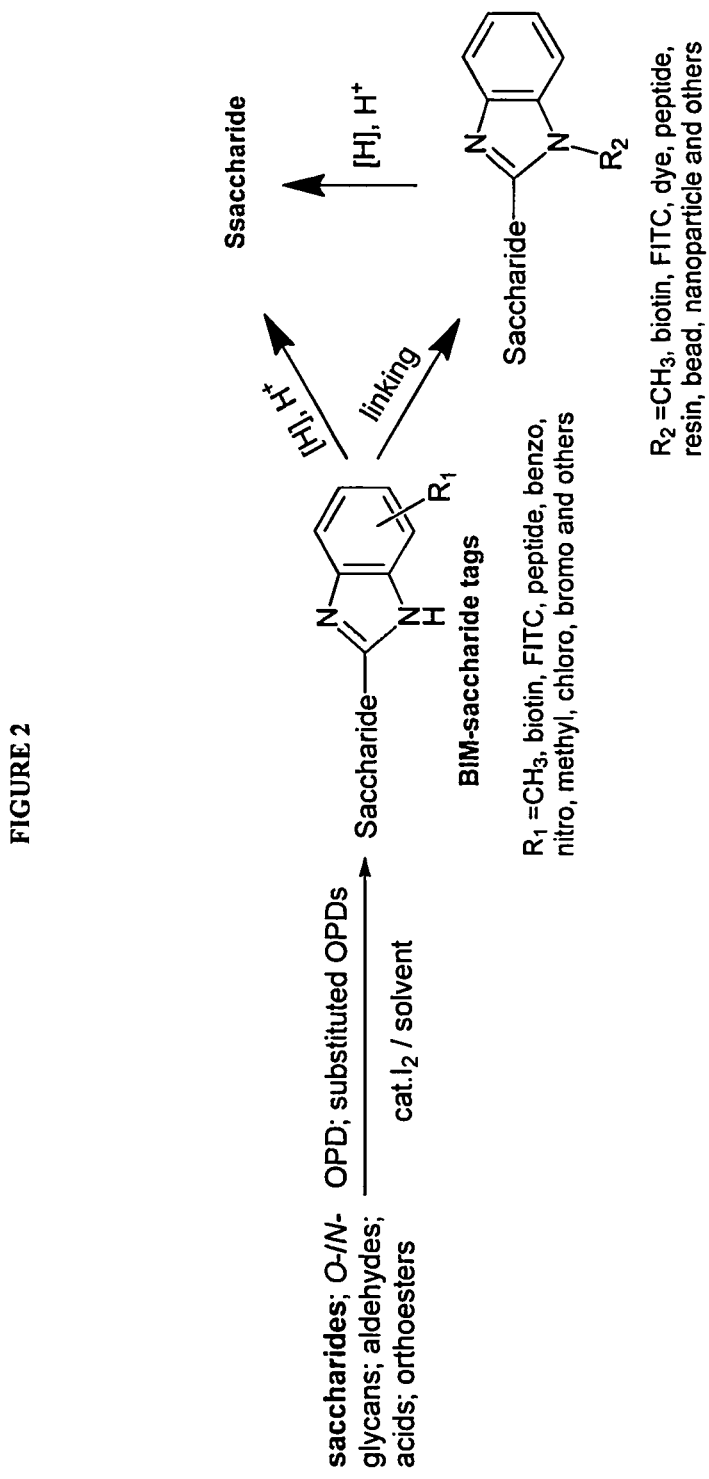
FIG. 2 shows a schematic diagram of a method of preparation of removable saccharide-BIM tags and conjugated saccharide-R$_2$-BIM tags.

Tagging of saccharide by tagging reagents, OPD or substituted OPDs, can be achieved by iodine catalytic oxidation condensation of saccharide and OPD as shown in FIG. 2. Conjugation of saccharide-BIM at 1H-position with R$_2$ (solid support, CH$_3$, dye, peptide etc.) can be achieved by N-alkylation. The saccharide-BIM tags and R$_2$-linked saccharide-R$_2$-BIMs can be reversed back to native saccharide by reduction and hydrolysis.

In some embodiments, saccharide-BIMs described herein comprise fucose+OPD, N-acetylgalactosamine+OPD, glucuronic acid+OPD, galacturonic acid+OPD, Globo H+OPD, GD2+OPD, GD3+OPD, GD1a+OPD, GQ1b+OPD, GT1b+OPD, GT1a+OPD, Gb3+OPD, Gb5+OPD, SSEA oligosaccharides+OPD, Fucosyl GM1+OPD, GM2+OPD, GM3+OPD, blood group antigens+OPD (A, B, O, H), Forssman antigens+OPD, Lewis a+OPD, Lewis b+OPD, Lewis X+OPD, Sialyl Lewis X+OPD, Lewis Y+OPD, lactose based O-glycans+OPD, N-acetylglucosamine core structures+OPD, sialyllactose+OPD, sialylated oligosaccharides+OPD, sulphated oligosaccharides+OPD, phosphated oligosaccharides+OPD, manno-oligosaccharides+OPD, cello-oligosaccharides+OPD, xylo-oligosaccharides+OPD, chito-oligosaccharides+OPD, malto-oligosaccharides+OPD, polysaccharides+OPD, aldehyde+OPD, carboxyl acid+OPD, or orthoacetate+OPD. Herein OPD composes aromatic ortho-diamine and substituted OPDs.

Any of saccharide-BIM can be further conjugated with (attached to) an acceptor (dye, peptide) or immobilized to solid support such as resin, nanoparticle, plate, chip etc. for saccharide analysis, image and other applications by N-alkylation at 1H-position of saccharide-BIMs.

As used herein, "conjugation", "conjugated" or "attached" means two entities are associated. The association between the two entities can be either direct or via a linker, such as a polymer linker. Conjugated or attached can include covalent or noncovalent bonding as well as other forms of association, such as entrapment (e.g. one entity on or within the other, or of either or both entities on or within a third entity, such as a micelle).

In one example, the saccharide-BIMs and conjugated saccharide-R-BIMs are capable to a detectable tag of saccharides, which is a compound that allows recognition, either directly or indirectly, the binding/conjugated to it such that the saccharide can be detected, measured, and/or qualified. Examples of such "detectable labels" are intended to include, but are not limited to, fluorescent labels, luminescent labels, colorimetric labels, enzymatic digestion, enzymatic markers, radioactive isotopes, and affinity tags such as biotin. Such labels can be used to the saccharide chemistry and glycomics, directly or indirectly, by conventional methods.

Detection of the present labeling saccharide tag (saccharide-BIMs or conjugated saccharide-R-BIMs) is performed using methods and reagents well known to those skilled in the art. A preferred method of detection of the invention is through the use of fluorescence. Fluorescence can be visualized with a variety of imaging techniques, including ordinary light or fluorescence microscopy, confocal laser-scanning microscopy, and flow cytometry.

In another example, conjugated saccharide-R-BIMs comprise saccharide-R$_2$-BIMs (Scheme2) and R$_2$ is a group producing by N-alkylation of saccharide-BIMs at 1H-position, in term of "conjugated saccharide-R-BIMs", thereby facilitating separation, purification and analysis of saccharides through wash, filter, centrifuge, MS determination, enzymatic digestion, protein binding, image etc.

The conjugated saccharide-R-BIMs (saccharide-R$_2$-BIMs) wherein R$_2$ is selected from the group consisting of solid support, resin, nanoparticle, plate, chip, dye, alkane, e.g. BODIPY Dye, Cascade Blue Dye, Coumarin, Fluorescein (FITC/FAM), Hapten, Lissamine Rhodamine B Dye, Oregon Green Dye, Texas Red Dye, azide, Marina Blue, Pacific Blue, Rhodamine 6G Dye, Rhodamine Green Dye, Rhodamine Red Dye, Tetramethylrhodamine, DNP, Digoxigenin, biotin, avidin, streptavidin, protein, luciferin, an anti-dye antibody, carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, DNP, biotin, digoxiginin, horse radish peroxidase (HRP), alkaline phosphatase (AP), β-galactosidase (GAL), glucose-6-phosphate dehydrogenase, β-N-acetylglucosamimidase, β-glucuronidase, invertase, Xanthine Oxidase, firefly luciferase, glucose oxidase, luminol, isoluminol, acridinium esters, 1,2-dioxetanes and pyridopyridazines.

In comparison with other saccharide tagging methods, the saccharide-BIMs and conjugated saccharide-R-BIMs has a number of advantages in saccharide detection. Applications of saccharide-BIM tags in glycomics are shown in FIG. 3.

Figure 3:
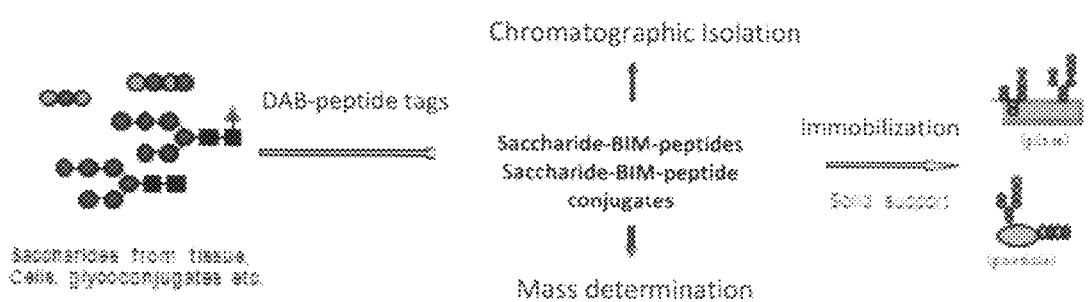
FIG. 3 shows an application of saccharide-BIMs and saccharide-R$_2$-BIMs (conjugated saccharide-BIMs) for conjugation to a solid support such as a particle or a plate.

As shown in FIG. 3, any of the saccharide-BIMs or conjugated saccharide-R-BIMs can be further conjugated with (attached to) a detectable label or immobilized to solid support such as resin, nanoparticle, plate, chip etc. for saccharide binding assay, imaging and other applications.

The present disclosure also provides a rapid method for purification, identification and derivation of saccharides and without destroyed glycans in glycomic studies, even when a tiny amount (less than 1 μmol) of saccharide is present in the sample.

As used herein, "conjugation", "conjugated" or "attached" means two entities are associated. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

In one aspect, the peptide in saccharide-BIM is attached to a detectable label, which is a compound that allows recognition, either directly or indirectly, the peptide conjugated to it such that the saccharide can be detected, measured, and/or qualified. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the peptide, directly or indirectly, by conventional methods.

Detection of the present labeling saccharide is performed using methods and reagents well known to those skilled in the art. A preferred method of detection of the invention is through the use of fluorescence. Fluorescence can be visualized with a variety of imaging techniques, including ordinary light or fluorescence microscopy, confocal laser-scanning microscopy, and flow cytometry.

N-Methylated Aldo-Imidazoles (Aldo-MeIMs) as Saccharide Tags

Figure 4:
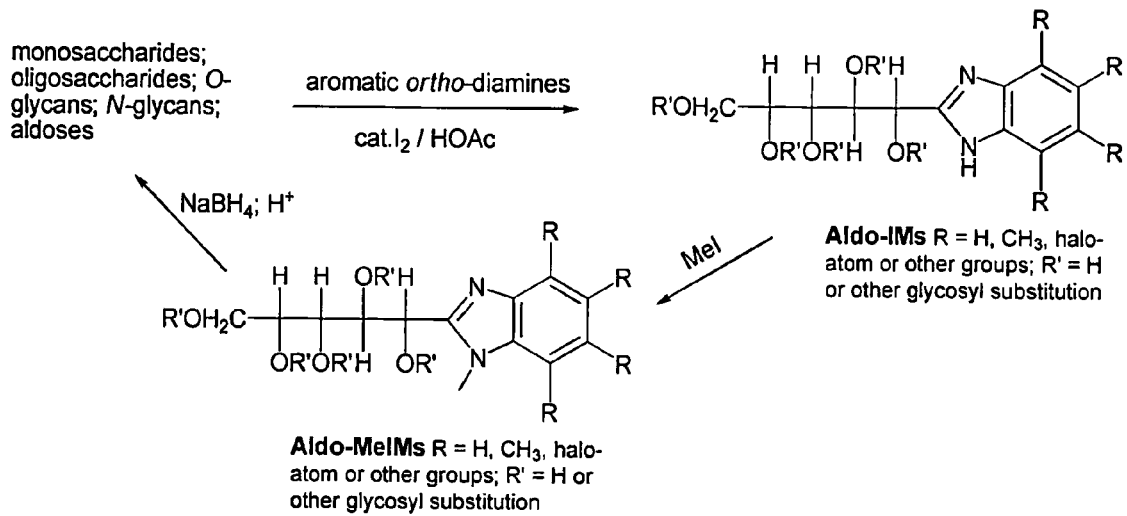
FIG. 4 shows a schematic diagram of a method of preparation of removable aldo-IM and aldo-MeIM saccharide tags.

In one aspect of the invention new saccharide tags, which are aldo-IM derivatives for saccharide labeling using synthetic approaches, are disclosed. Use of ortho-aromatic diamines as tags for aldoses and sialic acid has been demonstrated to be useful for saccharide analysis. N-methylated aldo-IMs (called aldo-MeIMs), the structures of which are shown in FIG. 4 below, can be further reduced back to untagged native saccharides. The recovery yield is high in this removable saccharide labeling method.

This is a novel example of acidic stable and removable tag using reducing-end labeling technology with high yields and convenience. After reduction of aldo-MeIMs by $NaBH_4$ and hydrolysis of the resulting product, the native saccharides were obtained and followed through an HPAEC-PAD analysis directly to evaluate the recovery yields of saccharides with no further purification.

The chemical preparation of N-methylated aldo-imidazoles (aldo-MeIMs) was achieved by using methyl iodide with aldo-IM, whereas aldo-IMs were prepared by iodine oxidation condensation of aldoses with aromatic ortho-diamines in DMSO at room temperature. The methodology of preparation of removable saccharide tags is shown in FIG. 4.

These aldo-IMs or aldo-MeIMs are useful in saccharide purification and determination. Using other commonly used methods (see FIG. 5), the tagged saccharides cannot be recovered in native form (ex. reduction amination and aldo-BINs) or are unstable in acidic conditions (ex. oximes and hydrazones). In comparison, aldo-IMs in accordance with the present invention are stable in both acidic and alkaline conditions and its aldo-MeIM derivatives can be reduced back to native saccharides. Therefore, saccharides, which are novel and tiny from biological sources, can be recovered for bioassays after chemical labeling. Therefore, through the use of the present invention, one may avoid the use of tagged saccharides, which might have different meanings than the native saccharides. Here, aldo-IMs and aldo-MeIMs were developed as removable and stable tags in glycan chemistry.

Figure 5:
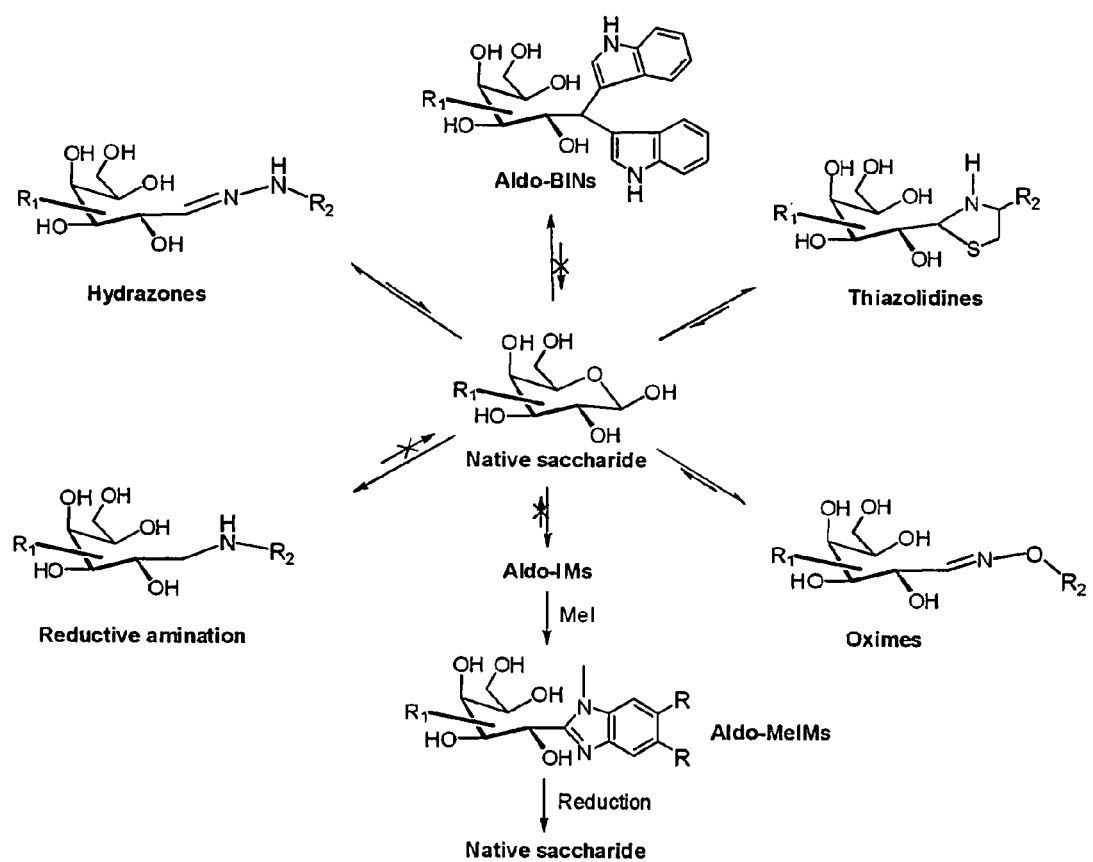
FIG. 5 shows methods for generating aldo-saccharide tags in saccharide labeling.

In addition, the aldo-MeIMs in accordance with the present invention are newly synthetic compounds for saccharide-tagging and have advantages on chromatographic analysis (such as HPLC, CE and MS) with their mother compound aldo-IMs. After reduction and hydrolysis of aldo-MeIMs in stepwise one-pot process, the native saccharides such as N-/O-glycans were obtained and the recovery yields can be analyzed by HPAEC-PAD or NMR directly with no further purification. For example, using HPAEC-PAD, a series of aldoses was recovered from aldo-MeIMs in high yield (Table 2) and these compounds have the same retention times and mass with original native aldoses (free aldose as standard). This removable saccharide tagging method is useful for biological investigation in comparison with other saccharide tagging methods as shown in FIG. 5.

TABLE 1

Measurement of the recovery yields of native saccharides from aldo-MeIMs by HPAEC-PAD[a]

| | Times | | | |
| --- | --- | --- | --- | --- |
| Aldose | Native aldose Peak time (min) | Aldo-IMs[a,b] Peak time (min) | Aldo-MeIMs[c,d] Peak time (min) | Recovery yield (%)[e] |
| Glucose | 12.1 | 7.3[a] | 4.5[c] | 92 |
| Glucose | 12.1 | 6.5[b] | 4.0[d] | 85 |
| Galactose | 8.7 | 7.1[a] | 4.7[c] | 88 |
| Mannose | 13.8 | 8.8[a] | 4.8[c] | 86 |
| Fucose | 4.8 | 2.2[a] | 2.0[c] | 90 |

[a]Peak retention times of aldo-NAIM (naphthylimidazole).
[b]Peak retention times of aldo-PIM (phenylimidazole).
[c]Peak retention times of aldo-MeNAIM.
[d]Peak retention times of aldo-MePIM.
[e]Dionex CarboPac PA-10 column was used, eluent 1.25 ml/min in 18 mM NaOH. The sample loading is set at 1 µM.

For advanced applications, aldo-IMs can be linked to peptides and other solid supports, such as resins, nano particles, plates, and chips, to enrich released glycans or to fish the proteins, which have interaction with aldo-IMs linked glycans. The glycans can be recovered from these materials. However, other glycan conjugated methods, such as reduction amination and C-glycosidation, do not recover native glycans from supports. Therefore, the method in accordance with the present invention provides a new tool in saccharide labeling.

Figure 6:
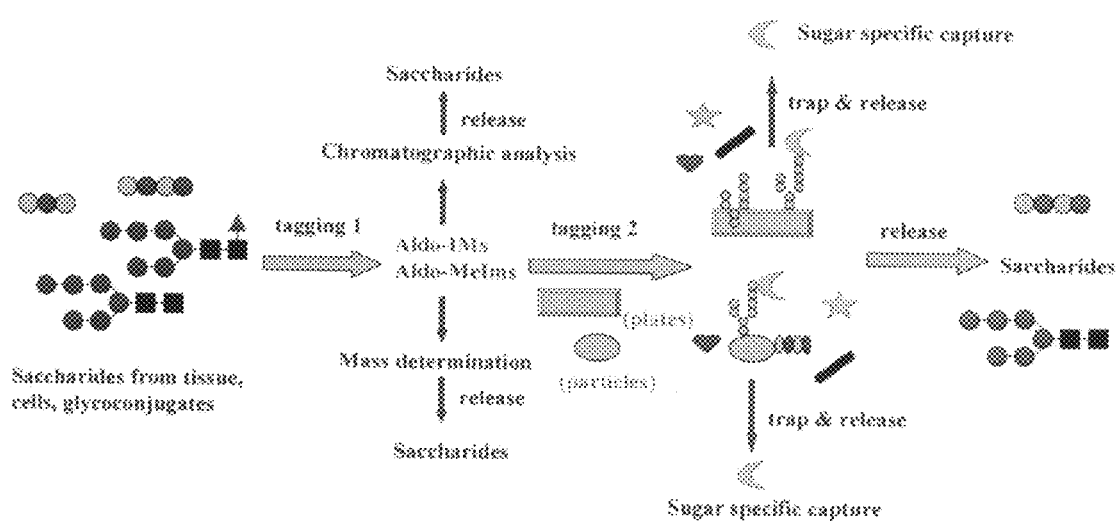
FIG. 6 shows applications of aldo-IM and aldo-MeIM tagged saccharides in glycomics.

The aldo-IM derivatives in accordance with the present invention can be applied as bioprobes and microarray to catch specific proteins and as removable tags for saccharides in glycomic studies. (FIG. 6).

Using these saccharide-tagging methods, some UV or fluorescence detectable labeled aldoses are first synthesized for saccharides analysis. These saccharide derivatized aldo-IMs or aldo-MeIMs can be distinguished easily by chromatography and mass determination. After reduction and hydrolysis of aldo-MeIMs, the novel native saccharides can be recovered. This is a new method for the conversion of unprotected and unmodified aldoses to aldo-MeIMs in carbohydrate chemistry. Aldoses, including those containing carboxyl and acetamido groups, undergo condensation reaction with aromatic vicinal diamines and through N-methylation to give the corresponding aldo-MeIMs in high yields. The advantages of this invention are described in FIG. 6 below. The combined use of this invention and chromatographic analysis thus provides a rapid method for purification, identification, and derivation of saccharides without destroyed glycans in glycomic studies, even when a tiny amount (less than 1 µmol) of saccharide is present in the sample.

In comparison with the commonly used reductive amination, these condensation reactions are easier to prepare and operate. Therefore, these aldo-IMs and aldo-MeIMs are useful reagents on saccharide labeling chemistry.

Ortho-Diaminobenzoic (DAB)-Peptide Tagged Saccharides

Accordingly, in one aspect the present disclosure relates to modified glycosides having the formula Y-X wherein Y represents a monosaccharide, oligosaccharide or polysaccharide subunits, in which the subunit is linked in a linear or branch chain by glycosidic linkages, and wherein X represents a tagging moiety comprising an ortho-diaminobenzoic (DAB)-peptide.

Disclosed herein are 3,4-diaminobenzoic (DAB)-peptide and the 3,4-diaminobenzoic (DAB)-peptide conjugated function molecules used as taggers to tag a saccharide at a reducing end of the saccharide to comprise a benzimidazole unit (saccharide-BIM-peptide or saccharide-BIM-peptide conjugated function molecules). Tagged saccharide can be generated by coupling an ortho-diaminobenzoic (DAB)-peptide tagging agent.

Disclosed herein are modified glycosides, the composition comprising (1) a monosaccharide, oligosaccharide or polysaccharide subunit, the subunit is linked in a linear or branch chain by glycosidic linkages, and (2) a tagging moiety.

The tagging moiety comprises an ortho-substituted, diamino-aromatic compound. In different embodiments of the invention the ortho-substituted, diamino-aromatic compound is 1,2-diaminobenzene (also known as ortho-phenylenediamine; OPD), 3,4-diaminobenzoic acid or 2,3-diaminopyridine. In a preferred aspect, the tagging moiety comprises 3,4-diaminobenzoic acid peptide (DAB-peptide) conjugate.

In some embodiments, the ortho-diaminobenzoic-peptide tagging agent is selected from the group consisting of DAB-6His, DAB-3His, DAB-Lys (biotin), DAB-Lys (FITC), DAB-Lys-resin.

In some embodiments, the DAB-peptide is generated by condensing a peptide or a functional label-conjugated peptide with N-Boc-diaminobenzoic acid by solid phase peptide synthesis or other chemical process.

The tagging moiety can be made by any conventional methods, e.g., standard methods of solid phase peptide synthesis or chemical synthesis well known to any one of ordinary skill in the art. For example, histidine, lysine, and functional molecule-conjugated peptides (e.g. biotin, fluorescent dyes, proteins etc.) can be condensed with N-Boc-2,3-diaminobenzoic acid (DAB) though amide bond formation by peptide synthesis.

The term "peptide" used herein refers to a polymer composed of one or more amino acid monomers and is shorter than a protein. Preferably, each of the cancer-targeting peptides described herein includes up to 50 (e.g., up to 10 or 20) amino acids. In some examples, the cancer-targeting peptides each contain 4-20 amino acid residues (e.g., 4-10, 6-10, 6-15, or 6-20 amino acid residues). These peptides can contain naturally-occurring amino acid residues, or modified amino acids. In one example, either the N-terminus or the C-terminus of a cancer-targeting peptide is modified, e.g., containing an —$NH_2$ group at the C-terminus.

The peptides may be synthesized by solid phase chemistry techniques following the procedures described by Steward et al. in Solid Phase Peptide Synthesis, 2nd Ed., Pierce Chemical Company, Rockford, Ill., (1984) using a Rainin PTI Symphony synthesizer. For solid phase peptide synthesis, techniques may be found in Stewart et al. in "Solid Phase Peptide Synthesis", W. H. Freeman Co. (San Francisco), 1963 and Meienhofer, Hormonal Proteins and Peptides, 1973. For classical solution synthesis, see for example Schroder et al. in "The Peptides", volume 1, Acacemic Press (New York). In general, such methods comprise the sequential addition of one or more amino acids or suitably protected amino acids to a growing peptide chain on a polymer. Normally, either the amino or carboxyl group of the first amino acid is protected by a suitable protecting group. The protected and/or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

The tagging agents, DAB-peptides, described herein can be used as detectable labels and are capable of for labeling saccharides at reducing end to form saccharide-DAB-peptides, thereby facilitating saccharide purification and analysis. In addition, DAB-peptides conjugated saccharides can increase ionization ability of saccharides, thereby improving sensitivity in MS analyses.

In some aspects the 3,4-diaminobenzoic acid (DAB) itself can be converted to a detectable moiety when it is enzymatically oxidized by horse radish peroxidase and hydrogen peroxide or urea peroxide to yield a fluorophore.

Figure 7:
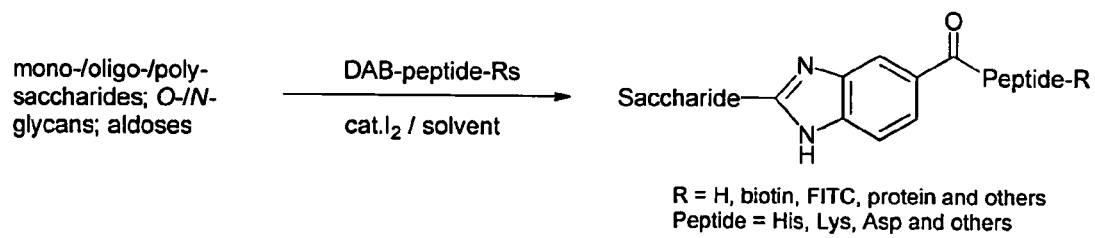
FIG. 7: Schematic view of conjugation of saccharide to tagging agents, DAB-peptides and DAB-peptide-Rs, achieved by iodine catalytic oxidation condensation of saccharide and DAB-peptides or DAB-peptide-Rs.

Conjugation of saccharide to tagging agents, DAB-peptides and DAB-peptide-Rs, can be achieved by iodine catalytic oxidation condensation of saccharide and DAB-peptides or DAB-peptide-Rs as shown in FIG. 7.

In some embodiments, saccharide-DAB-peptides described herein comprise saccharide-DAB-6His, saccharide-DAB-6His-resin, saccharide-DAB-3His, saccharide-DAB-3His-resin, saccharide-DAB-Lys-biotin, saccharide-DAB-Lys-FITC, saccharide-DAB-6His, saccharide-DAB-3His, saccharide-DAB-Lys-biotin, saccharide-DAB-Lys-resin.

In another example, saccharide-DAB-peptides comprise saccharide-DAB-$(His)_6$ and saccharide-DAB-$(His)_3$ bound to Ni column, thereby facilitating separation and purification of saccharides through immobilized metal affinity chromatography (IMAC). In addition, saccharide-DAB-peptide-resin comprise saccharide-DAB-(His)-6-resin and saccharide-DAB-$(His)_3$-resin thereby facilitating separation and purification of saccharides washed, filtered or centrifuged.

Figure 8:
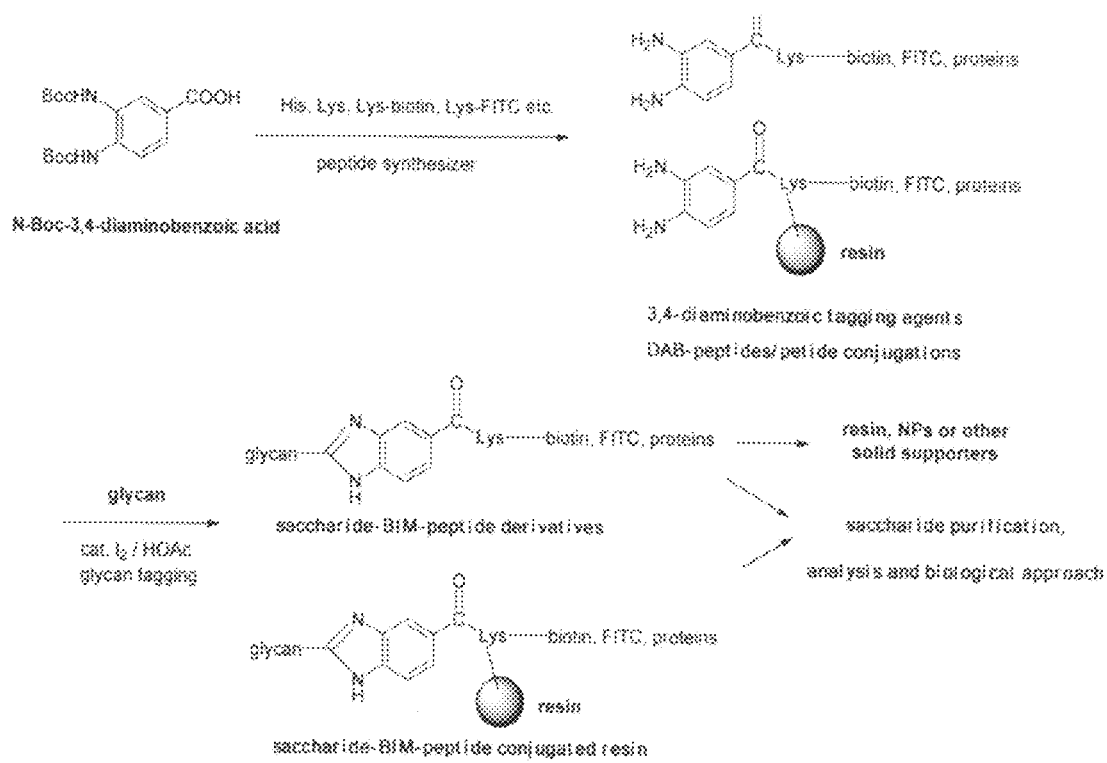
FIG. 8: Schematic view of preparation of DAB-peptide tagging reagents and DAB-peptide conjugated resin or other bio-molecules tagging reagents for saccharide tagging.

Preparation of DAB-peptide tagging reagents and DAB-peptide conjugated resin or other bio-molecules tagging reagents for saccharide tagging is shown in FIG. 8.

Figure 9:
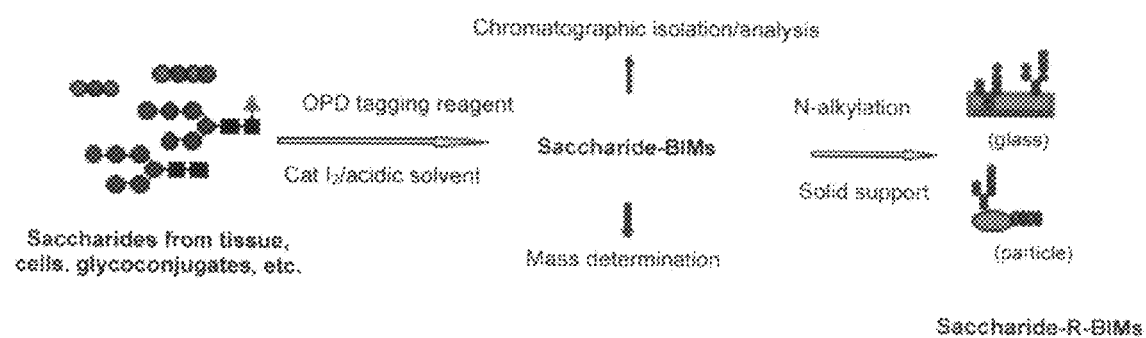
FIG. 9: Applications of saccharide-DAB-peptides in glycomics.

Comparison with other saccharide tagging methods, the saccharide-DAB-peptides have a number of advantages in saccharide detection. Applications of saccharide-DAB-peptides in glycomics are shown in FIG. 9.

The present disclosure also provides a rapid method for purification, identification and derivation of saccharides and without destroyed glycans function in glycomic studies, even when a tiny amount (less than 1 µmol) of saccharide is present in the sample.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Chemical Structures of Saccharides

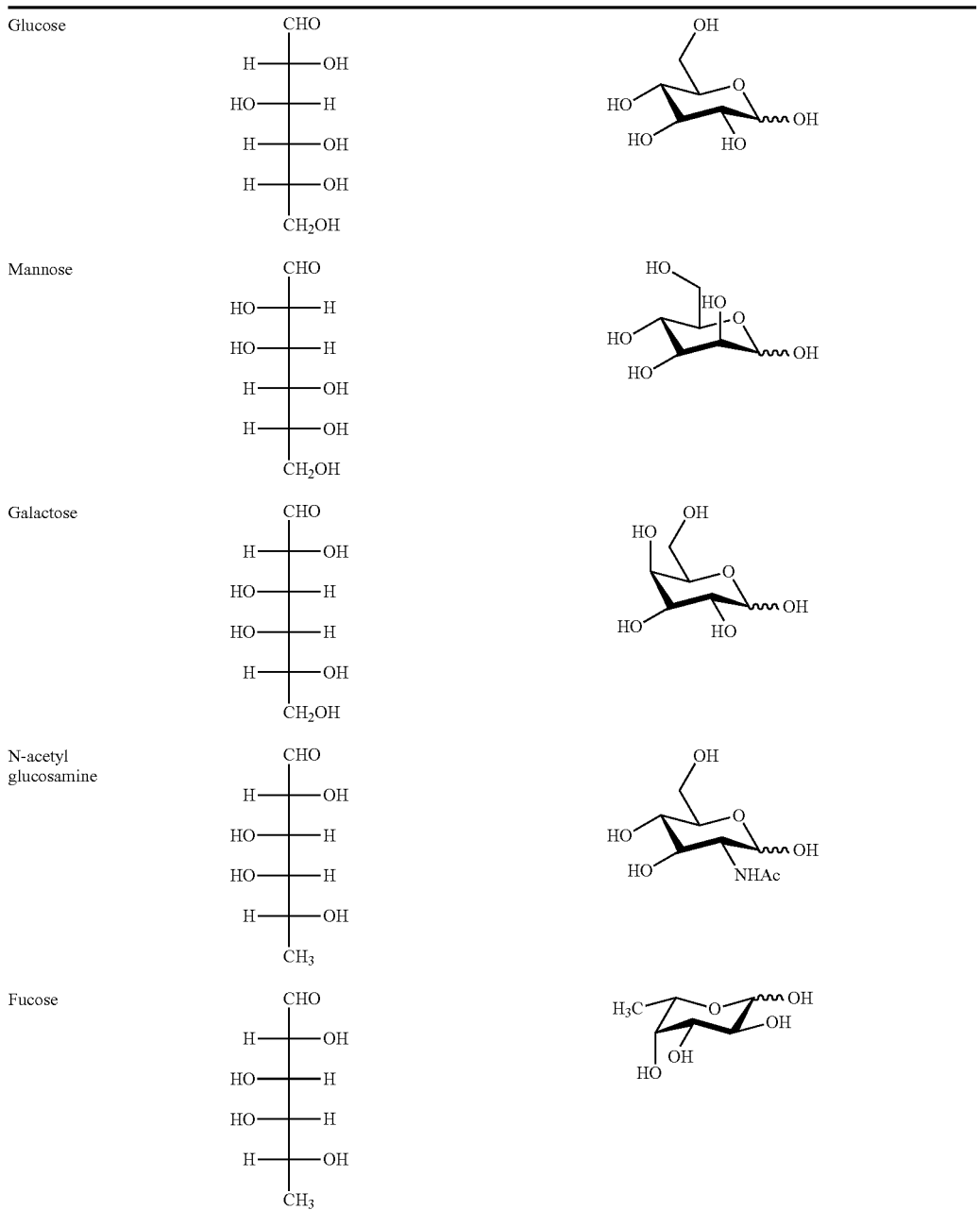

-continued
Lactose
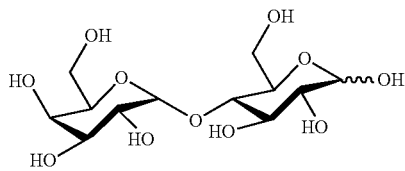
Maltose
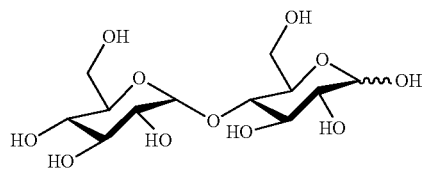
Globo-H
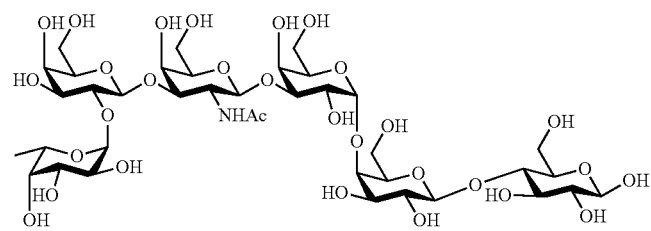
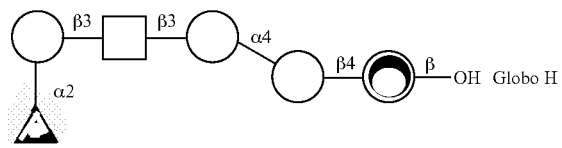 Globo H
GD2 oligosaccharide component
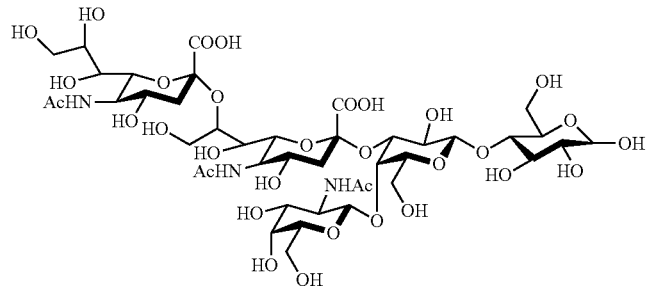
[GalNAcβ1→4(NeuAcα2→8NeuAcα2→3)Galβ1→4Glc]
Cellohexose
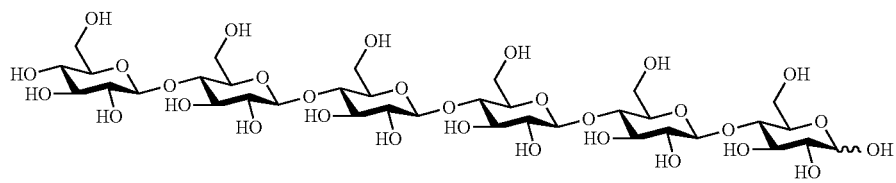
Polysaccharides
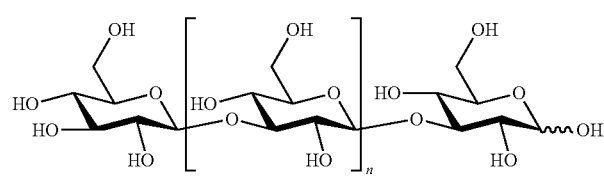
$n > 8, 10, 20$

Example 2

Synthesis of N-Boc-3,4-Diaminobenzoic Acid (N-Boc-Dab)

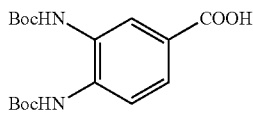

N-Boc (N-tert-butoxy carbonyl) protected 3,4-diaminobenzoic acid precursor (3,4-DAB) was prepared by reacting 3,4-diaminobenzoic acid (1.52 g, 10 mmol) and di-tert-butoxy dicarbonate ((t-Boc)$_2$O, 6.55 g, 30 mmol) with triethylamine (NEt$_3$; 7.0 mL, 60 mmol) in chloroform (CHCl$_3$, 200 mL) at room temperature (25° C.) stirring for overnight (24 h). The resulting solution was extracted with water, dried with Na$_2$SO$_4$ to give N-Boc-3,4-diaminobenzoic acid (2.0 g, 79%) as a brown powder. $^1$H NMR (600 MHz, d-MeOH) δ 7.96 (s, 1H, ArH), 7.75 (dd, 1H, J=8.4, 1.9 Hz, ArH), 7.60 (d, 1H, J=8.4, 1.9 Hz, ArH), 4.80 (brs, 2H, NH), 1.52 (s, 18H, CH$_3$). $^{13}$C NMR (150 MHz, d-MeOH) δ 173.2, 156.4, 155.5, 135.7, 133.6, 130.3, 127.9, 127.8, 123.6, 81.7, 81.6, 28.8, 28.7. Mass of N-Boc-DAB (C$_{17}$H$_{24}$N$_2$O$_6$; 352.4 Da) was measured.

Example 3

Synthesis 3,4-diaminobenzoic-(His)$_3$ Tagger

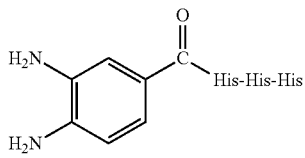

Figure 10:
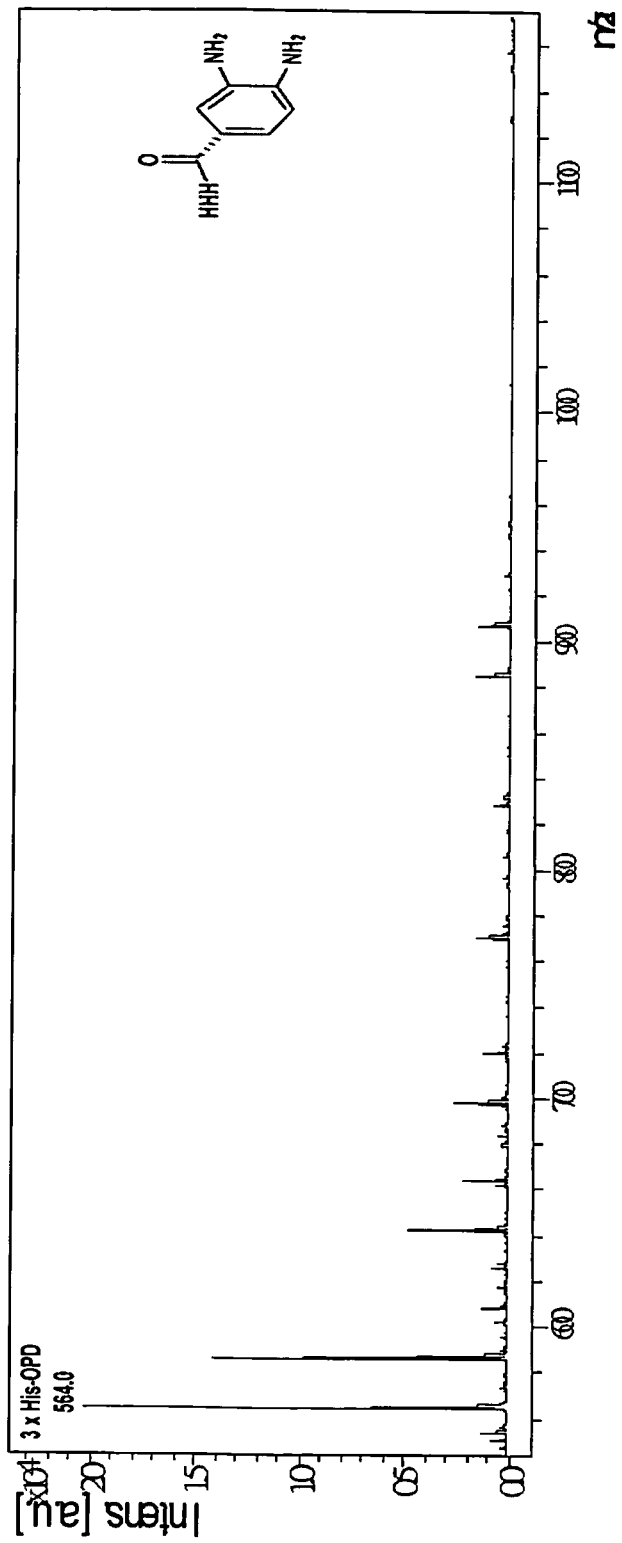
FIG. 10: The MS of 3,4-diaminobenzoic-(His)$_3$ tagger ($C_{25}H_{29}N_{11}O_5$; 564.0 Da) measured by MALDI-TOF MS.

The N-Boc (N-tert-butoxy carbonyl) protected 3,4-diaminobenzoic precursor (N-Boc-DAB), which was obtained by block amino group on DAB using di-tert-butyl dicarbonate (t-Boc$_2$O), was added 3 histidine units by solid phase peptide synthesis (ABI 433A Peptide Synthesizer) and followed hydrolysis to give 3,4-diaminobenzoic-(His)$_3$ tagger (DAB-His-His-His). The MS of 3,4-diaminobenzoic-(His)$_3$ tagger (C$_{25}$H$_{29}$N$_{11}$O$_5$; 564.0 Da) was measured by MALDI-TOF MS as shown in FIG. 10.

Example 4

Synthesis of 3,4-diaminobenzoic-(His)$_3$-Resin Tagger

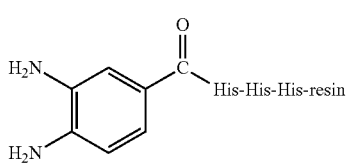

The N-Boc (N-tert-butoxy carbonyl) protected 3,4-diaminobenzoic precursor (N-Boc-DAB), which was obtained by block amino group on DAB using di-tert-butyl dicarbonate (t-Boc), was added 3 histidine units by solid phase peptide synthesis with TentaGal resin to give 3,4-diaminobenzoic-(His)$_3$-resin tagger (DAB-His-His-His-resin).

Example 5

Synthesis 3,4-diaminobenzoic-(His)$_6$ Tagger

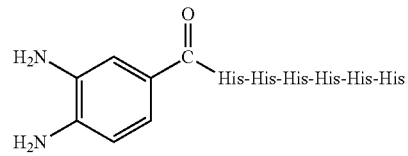

Figure 11:
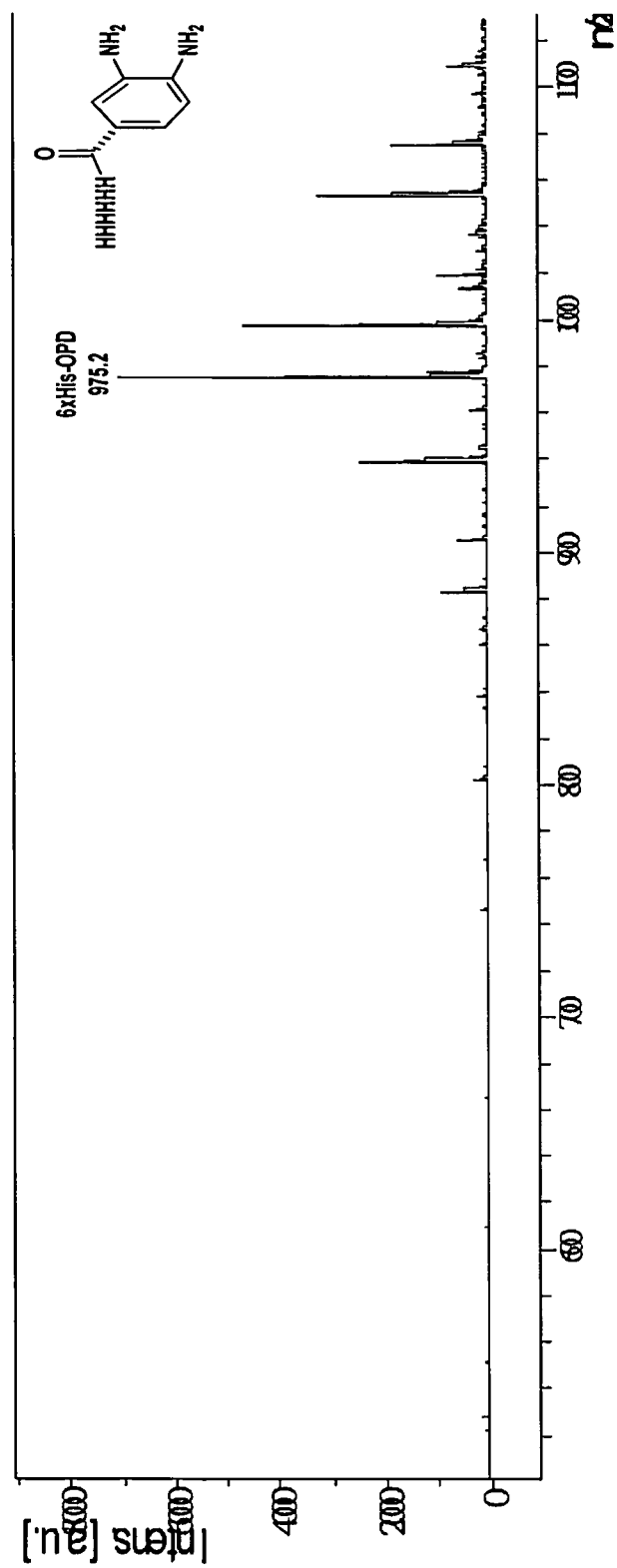
FIG. 11: The MS of 3,4-diaminobenzoic-(His)$_6$ tagger ($C_{43}H_{50}N_{20}O_8$; 975.2 Da) measured by MALDI-TOF MS.

The N-Boc (N-tert-butoxy carbonyl) protected 3,4-diaminobenzoic precursor (N-Boc-DAB), which was obtained by block amino group on DAB using di-tert-butyl dicarbonate (t-Boc), was added 6 histidine units by solid phase peptide synthesis (ABI 433A Peptide Synthesizer) and followed hydrolysis to give 3,4-diaminobenzoic-(His)$_6$ tagger (DAB-His-His-His-His-His-His). The MS of 3,4-diaminobenzoic-(His)$_6$ tagger (C$_{43}$H$_{50}$N$_{20}$O$_8$; 975.2 Da) was measured by MALDI-TOF MS as shown in FIG. 11.

Example 6

Synthesis of 3,4-diaminobenzoic-(His)-6-Resin Tagger

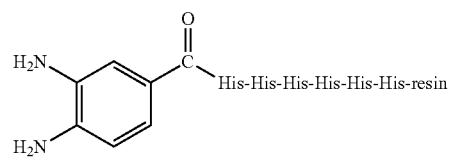

The N-Boc (N-tert-butoxy carbonyl) protected 3,4-diaminobenzoic precursor (N-Boc-DAB), which was obtained by block amino group on DAB using di-tert-butyl dicarbonate (t-Boc), was added 6 histidine units by solid phase peptide synthesis with TentaGal resin to give 3,4-diaminobenzoic-(His)$_6$-resin tagger (DAB-His-His-His-His-His-His-resin).

Example 7

Synthesis of 3,4-diaminobenzoic-Lys-(Biotin) Tagger

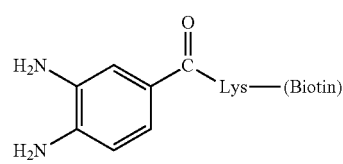

The N-Boc (N-tert-butoxy carbonyl) protected 3,4-diaminobenzoic precursor (N-Boc-DAB), which was obtained by block amino group on DAB using di-tert-butyl dicarbonate (t-Boc), was added lysine-(Biotin) unit by solid phase peptide synthesis (ABI 433A Peptide Synthesizer) and followed hydrolysis to give 3,4-diaminobenzoic-lysine-(Biotin) tagger (DAB-Lys-(Biotin)). The MS of 3,4-diaminobenzoic-lysine-(Biotin) tagger (506.3 Da) was measured by MALDI-TOF MS.

Example 8

Synthesis of maltohexose-DAB

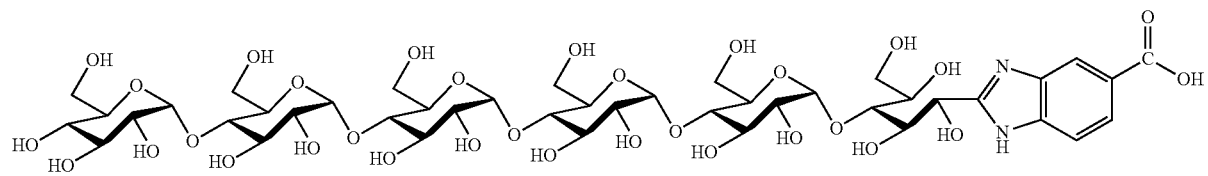

Figure 12:
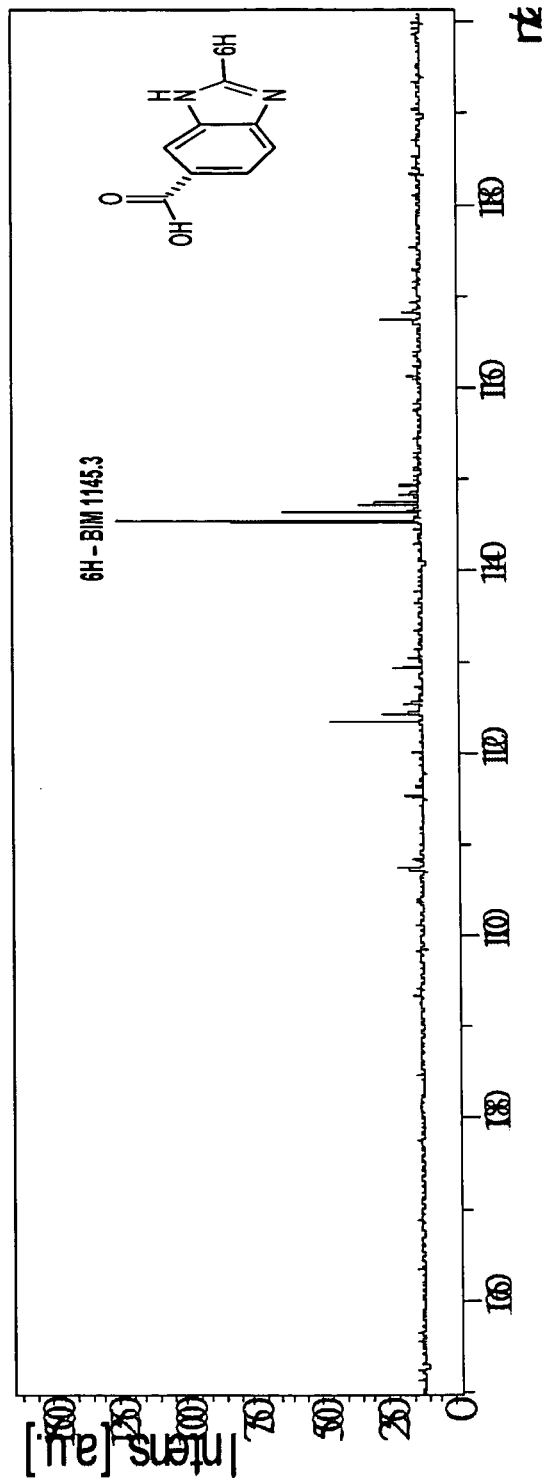
FIG. 12: The molecular weight of condensed maltohexose-DAB obtained ($C_{43}H_{66}N_2O_{32}Na$; 1145.3 Da) by MALDI-TOF MS.

The native maltohexose (6H or G6; 1.0 mg) was tagged with 3,4-diaminobenzoic acid (DAB; 1.0 mg) in presence of catalytic amount of iodine at acetic acid solution to form the maltohexose-DAB product. The molecular weight of condensed maltohexose-DAB was obtained ($C_{43}H_{66}N_2O_{32}Na$; 1145.3 Da) by MALDI-TOF MS as shown in FIG. 12.

Example 9

Synthesis of maltotetraose-DAB-(His)$_6$

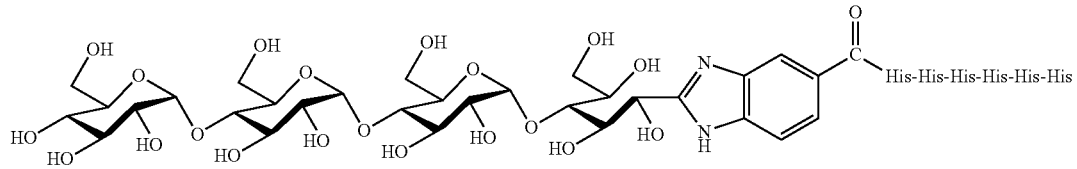

Figure 13:
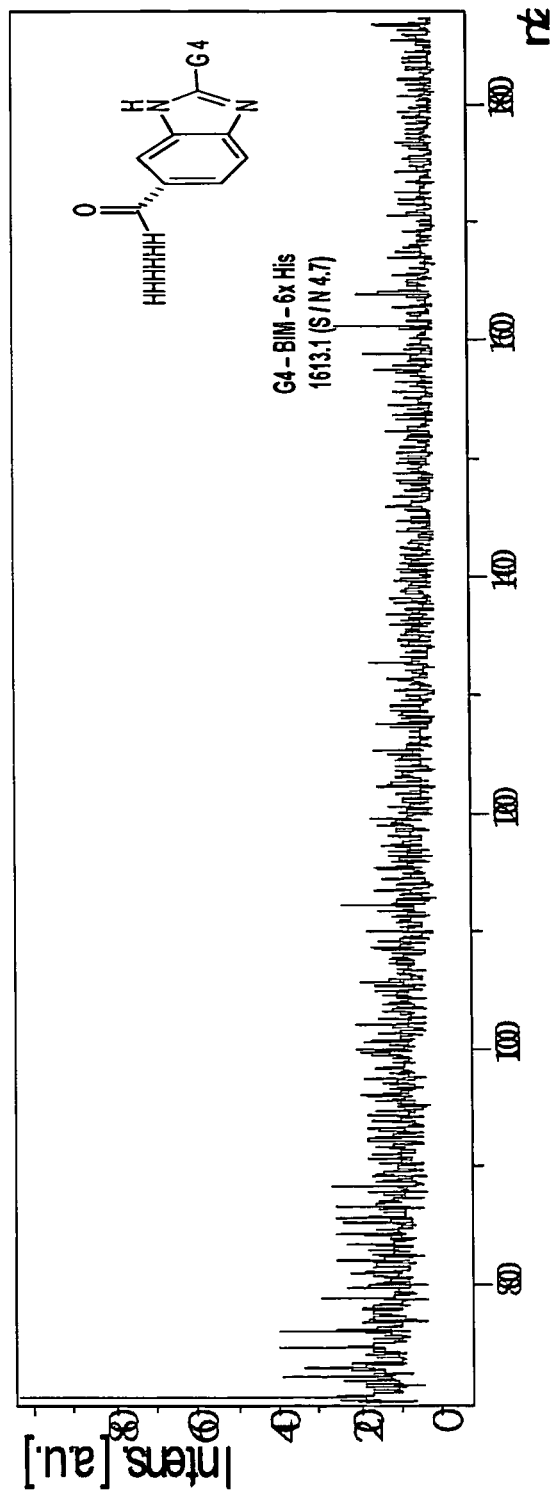
FIG. 13: The molecular weight of condensed maltotetraose-DAB-(His)$_6$ obtained ($C_{67}H_{88}N_{20}O_{28}$; 1613.1 Da) by MALDI-TOF MS.

The native maltotetraose (G4; 1.0 mg) was tagged with 3,4-diaminobenzoic-(His)$_6$ (DAB-(His)$_6$; 1.0 mg) in presence of catalytic amount of iodine at acetic acid solution to form the maltotetraose-DAB-(His)$_6$ product. The molecular weight of condensed maltotetraose-DAB-(His)$_6$ was obtained ($C_{67}H_{88}N_{20}O_{28}$; 1613.1 Da) by MALDI-TOF MS as shown in FIG. 13.

Example 10

Synthesis of maltohexose-DAB-(His)$_3$

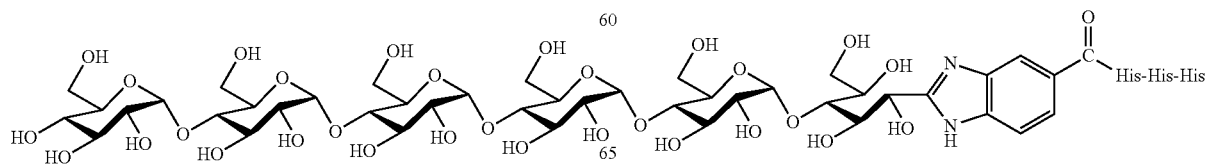

Figure 14:
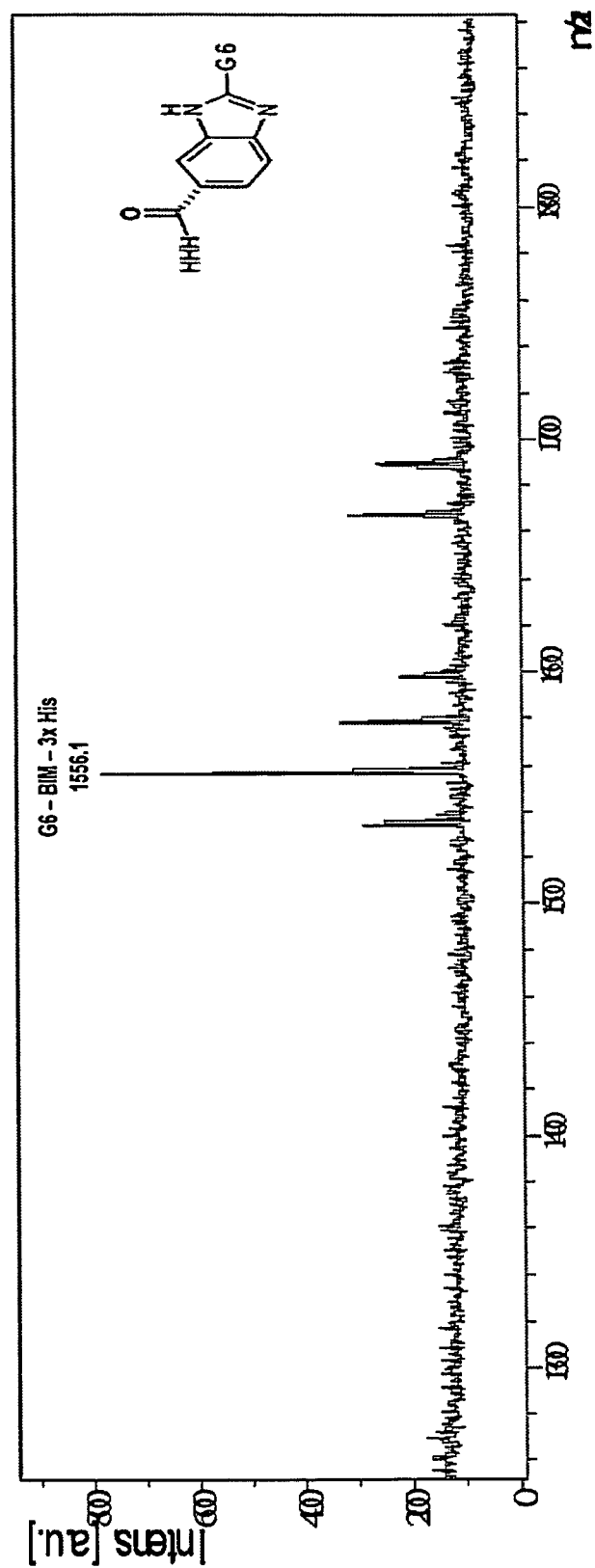
FIG. 14: The molecular weight of condensed maltohexose-DAB-(His)$_3$ obtained ($C_{61}H_{87}N1_1O_{35}Na$; 1556.1 Da); 1556.1 Da) by MALDI-TOF MS.

The native maltohexose (G6; 1.0 mg) was tagged with 3,4-diaminobenzoic-(His)₃ (DAB-(His)₃; 1.0 mg) in presence of catalytic amount of iodine at acetic acid solution to form the maltohexose-DAB-(His)₃ product. The molecular weight of condensed maltohexose-DAB-(His)₃ was obtained ($C_{61}H_{87}N_{11}O_{35}Na$; 1556.1 Da) by MALDI-TOF MS as shown in FIG. 14.

Example 11

Synthesis of maltohexose-DAB-(His)₆

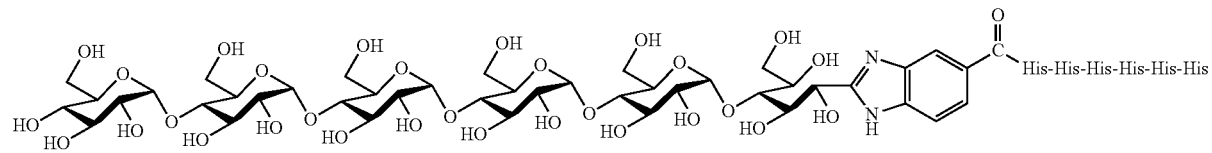

Figure 15:
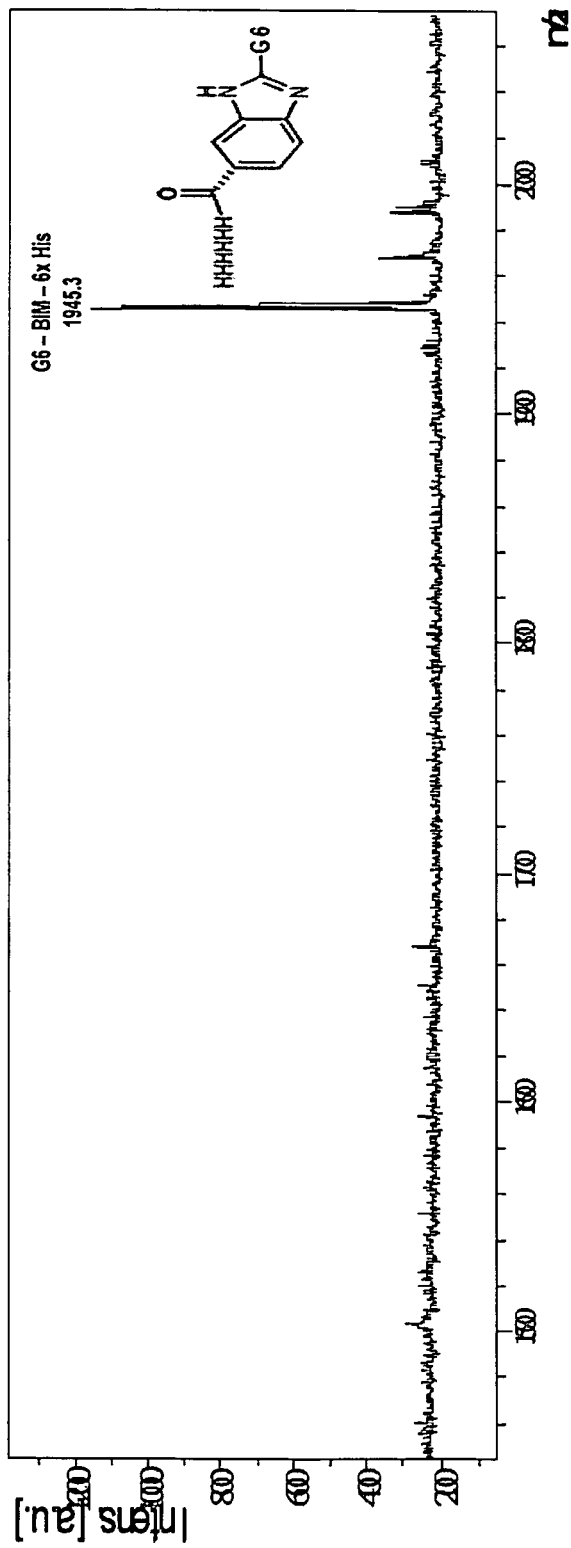
FIG. 15: The molecular weight of condensed maltohexose-DAB-(His)$_6$ obtained ($C_{79}H_{108}N_{20}O_{38}$; 1945.3 Da) by MALDI-TOF MS.

The native maltohexose (G6; 1.0 mg) was tagged with 3,4-diaminobenzoic-(His)₆ (DAB-(His)₆; 1.0 mg) in presence of catalytic amount of iodine at acetic acid solution to form the maltohexose-DAB-(His)₆ product. The molecular weight of condensed maltohexose-DAB-(His)₆ was obtained ($C_{79}H_{108}N_{20}O_{38}$; 1945.3 Da) by MALDI-TOF MS as shown in FIG. 15.

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

We claim:

1. A composition comprising a modified glycoside having the formula:

Y~X, wherein Y represents a monomeric or polymeric form of a saccharide, and wherein X represents a reversibly conjugated tagging moiety comprising an N-methylated aldo-imidazole (MeIM) having the structure

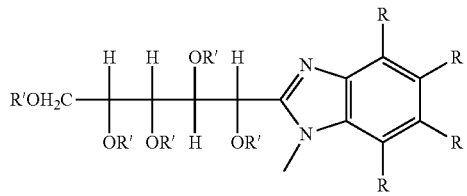

wherein R=H, CH₃, or a halo-atom, R'=H, and wherein the R' attached to the third carbon atom from the carbon atom of the aldose conjugated to the benzimidazole of the MeIM represents H, or a bond linking to an anomeric carbon of a monosaccharide or a polysaccharide.

2. The composition of claim 1 wherein the saccharide subunit, Y, is the same or different and is selected from the group consisting of glucose, galactose, fructose, ribulose, mannose, ribose, arabinose, xylose, lyxose, allose, altrose, gulose, rhamnose, arabinose, fucose, N-acetylgalactosamine, glucuronic acid, galacturonic acid, Globo H, GD2, GD3, GD1a, GQ1b, GT1b, GT1a, Gb3, Gb5, SSEA oligosaccharides, Fucosyl GM1, GM2, GM3, blood group antigens (A, B, O, H), Forssman antigens, Lewis a, Lewis b, Lewis X, Sialyl Lewis X, Lewis Y, lactose based O-glycans, N-acetylglucosamine core structures, sialyllactose, sialylated oligosaccharides, sulphated oligosaccharides, phosphated oligosaccharides, manno-oligosaccharides, cello-oligosaccharides, xylo-oligosaccharides, chito-oligosaccharides, malto-oligosaccharides, and malto-polysaccharides, wherein the subunits may be the same or different when present in polymeric form.

3. The composition of claim 1 wherein X further comprises a detectable label suitable for mass spectrometric (MS) analysis, saccharide purification, photometric analysis or enzymatic analysis.

4. The composition of claim 3, wherein the detectable label is selected from the group consisting of solid support, resin, nanoparticle, plate, chip, dye, alkane, e.g. BODIPY Dye, Cascade Blue Dye, Coumarin, Fluorescein (FITC/FAM), Hapten, Lissamine Rhodamine B Dye, Oregon Green Dye, Texas Red Dye, azide, Marina Blue, Pacific Blue, Rhodamine 6G Dye, Rhodamine Green Dye, Rhodamine Red Dye, Tetramethylrhodamine, DNP, Digoxigenin, biotin, avidin, streptavidin, protein, luciferin, an anti-dye antibody, 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, R-phycoerythrin (RPE) allophycoerythrin (APC), Texas Red, Princeton Red, Green fluorescent protein (GFP) coated CdSe nanocrystallites, DNP, biotin, digoxigenin, horse radish peroxidase (HRP), alkaline phosphatase (AP), β-galactosidase (GAL), glucose-6-phosphate dehydrogenase, β-N-acetylglucosamimidase, β-glucuronidase, invertase, Xanthine Oxidase, firefly luciferase, glucose oxidase, luminol, isoluminol, acridinium esters, 1,2-dioxetanes and pyridopyridazines.

5. The composition of claim 1, wherein X further comprises a detectable label selected from a fluorescent label, an enzyme label, a radioisotope, a chemiluminescent label, a bioluminescent label, a polymer, a metal particle, a hapten, an antibody, and a dye.

6. The composition of claim 1, wherein the modified glycoside, Y-X, is coupled to a solid support and further wherein the solid support is selected from a test paper, resin, a bead, a planar support, a glass slide, a polycarbonate slide, a nanoparticle, a chromatographic medium, a magnetic particle and a metal.

7. The composition of claim 6, wherein the solid support is suitable for identification, isolation or diagnosis of the saccharide.

\* \* \* \* \*